United States Patent
Lahr et al.

(10) Patent No.: US 12,291,224 B2
(45) Date of Patent: May 6, 2025

(54) SYSTEM AND METHOD FOR TRACKING AND VERIFICATION OF QUESTIONABLE CONTROL INPUTS BY INCAPACITATED OPERATORS

(71) Applicant: Rockwell Collins, Inc., Cedar Rapids, IA (US)

(72) Inventors: Weston J. Lahr, Sherwood, OR (US); Cheyenne B. Matthews, Marion, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 157 days.

(21) Appl. No.: 17/992,312

(22) Filed: Nov. 22, 2022

(65) Prior Publication Data

US 2024/0166225 A1    May 23, 2024

(51) Int. Cl.
| | | |
|---|---|---|
| *B60W 50/10* | (2012.01) | |
| *A61B 5/16* | (2006.01) | |
| *A61B 5/18* | (2006.01) | |
| *G09B 19/16* | (2006.01) | |

(52) U.S. Cl.
CPC .............. *B60W 50/10* (2013.01); *A61B 5/163* (2017.08); *A61B 5/18* (2013.01); *G09B 19/165* (2013.01)

(58) Field of Classification Search
CPC .......... B60W 50/10; A61B 5/163; A61B 5/18; A61B 5/165; G09B 19/165; B64D 45/00; B64D 45/0056
See application file for complete search history.

(56) References Cited

U.S. PATENT DOCUMENTS

| | | |
|---|---|---|
| 4,775,116 A | 10/1988 | Klein |
| 9,637,133 B1 | 5/2017 | McCusker et al. |
| 9,919,712 B1 | 3/2018 | Doyen et al. |
| | (Continued) | |

FOREIGN PATENT DOCUMENTS

EP    2647959 B1    5/2020

OTHER PUBLICATIONS

Bailey et al, R. An Assessment of Reduced Crew and Single Pilot Operations in Commercial Transport Aircraft Operations, Google Scholar, 2017 IEEE/AIAA 36th Digital Avionics Systems Conference (DASC), Nov. 2017, pp. 1-15. (Year: 2017).*

(Continued)

*Primary Examiner* — Russell Frejd
(74) *Attorney, Agent, or Firm* — Suiter Swantz IP (57) ABSTRACT

An aircraft-based system for tracking and verifying control inputs from potentially incapacitated pilot stores to memory expected control input sets, e.g., control procedures for controlling an aircraft through segments of a flight plan. When pilot monitors indicate a state of potential incapacitation of a pilot (e.g., fatigue, unresponsiveness, hypoxia), the control input tracking system records any control inputs submitted via the flight deck controls by the incapacitated pilot, reviewing each recorded control input compared to expected control inputs (e.g., for the current flight segment). When a recorded control input sufficiently deviates from the corresponding expected control input (e.g., such that aircraft safety or mission criticality may be affected), the pilot and/or flight crew may receive feedback alerting to the deviant control input (e.g., which may be overridden or which may require confirmation prior to execution).

20 Claims, 4 Drawing Sheets

(56) References Cited

U.S. PATENT DOCUMENTS

| | | |
|---|---|---|
| 10,102,773 B2 | 10/2018 | Towers et al. |
| 10,293,830 B2 | 5/2019 | Selvaraj et al. |
| 10,328,852 B2 | 6/2019 | Wilson et al. |
| 10,426,393 B2 | 10/2019 | Bosworth et al. |
| 2003/0163232 A1 | 8/2003 | Moretto |
| 2012/0215384 A1 | 8/2012 | Fritz |
| 2015/0123820 A1 | 5/2015 | Merle et al. |
| 2018/0364707 A1 | 12/2018 | Bosworth et al. |
| 2019/0023377 A1 | 1/2019 | Henderson et al. |
| 2019/0061772 A1 | 2/2019 | Prinz |
| 2020/0183382 A1* | 6/2020 | Schwindt ............. G08G 5/0052 |
| 2021/0034053 A1 | 2/2021 | Nikolic et al. |
| 2021/0188332 A1 | 6/2021 | Brooks et al. |
| 2021/0241654 A1 | 8/2021 | Onur et al. |
| 2022/0291680 A1* | 9/2022 | Schwindt ............... B64D 45/00 |

OTHER PUBLICATIONS

Liu et al, J. Cognitive Pilot-Aircraft Interface for Single-Pilot Operations, Google Scholar, Sciencedirect, Knowledge-based Systems, 2016, pp. 37-53. (Year: 2016).*

Martins et al, A. Toward Single Pilot Operations: A Conceptual Framework to Manage In-Flight Incapacitation, Google Scholar, 2021, pp. 1-9. (Year: 2021).*

European Search Report dated Mar. 12, 2024; European Application No. 23210976.9.

* cited by examiner

SYSTEM AND METHOD FOR TRACKING AND VERIFICATION OF QUESTIONABLE CONTROL INPUTS BY INCAPACITATED OPERATORS

BACKGROUND

Aircraft pilots (e.g., co-pilots, operators) may from time to time become incapacitated. For example, pilots may become temporarily incapacitated due to, e.g., fatigue, hypoxia, cognitive workload, or other physiological factors. If the pilot is part of a multi-member command crew, for example, physiological incapacity may be detected by a pilot monitor and the pilot seamlessly relieved as a pilot-in-command (PIC) by a co-pilot. However, even if the pilot is assisted by other command crew, an incapacitated pilot may be still be responsible for unintentional control inputs to various control systems of the aircraft. Unintentional control inputs may be minor or inconsequential: for example, a pilot may inadvertently deactivate a synthetic vision system (SVS) feed to a cockpit display, which is easily and quickly corrected and does not directly impede the safe flight of the aircraft. However, unintentional control inputs to safety-critical and/or irreversible control systems, e.g., a fire extinguisher system, may create an immediate hazard to the pilot, crew, and passengers aboard the aircraft.

Additionally, while pilot incapacity may take more mundane, non-physiological forms, these latter types of pilot incapacity may be every bit as hazardous. For example, in 2018 Air India Express Flight 611, a Boeing 737-800 bound for Dubai, took off from Trichy (Tiruchirappalli) Airport in Tamil Nadu. As the flight was granted takeoff clearance, the cabin crew set throttles to takeoff levels (98% thrust) and the captain placed his hands on the thrust levers in order to quickly close the throttles in the event of an aborted takeoff. As the aircraft accelerated toward takeoff, the captain's reclining seat backrest unexpectedly collapsed, causing the captain to inadvertently move his hand backward. As he did so, he unintentionally pulled the thrust levers back with him, reducing thrust from 98% to 77%. The Air India Express captain immediately handed temporary control of the aircraft over to the first officer while he recovered his position, but the first officer failed to confirm the position of the thrust levers as required by procedures for dealing with an incapacitated pilot. The captain successfully executed the takeoff upon regaining control of the aircraft, even though very little available runway remained. However, due to the reduction in thrust (and the short remaining runway) the aircraft struck a perimeter wall and an ILS antenna during liftoff, injuring a person on the ground and significantly damaging the aircraft. The aircraft continued toward Dubai, even when informed of the damage on the ground and the likely (and later confirmed) damage to the aircraft, until diverted to Mumbai for a safe landing. Subsequent investigations determined that 1) had the first officer immediately aborted the takeoff, sufficient runway remained for a successful abort, and 2) had the captain immediately increased thrust upon regaining command, the aircraft would have taken off safely and without incident. However, at no point did either the captain or the first officer appear to realize thrust levels had been reduced.

SUMMARY

In a first aspect, an aircraft-based control input tracking system is disclosed. In embodiments, the system is connected to the aircraft's control systems (e.g., flight deck controls) and to pilot monitors (e.g., tracking the situational awareness and physiological well-being of the pilot). The system includes memory for storing expected control input procedure sets (e.g., for controlling the operation of the aircraft through each segment of its flight plan; in some embodiments including procedures for co-pilots and/or flight crew for dealing with an incapacitated pilot). When the pilot monitor indicates an adverse incapacitation state of the pilot (e.g., potential or definite fatigue, hypoxia, unresponsiveness, or other like adverse physiological state), the system records control inputs submitted by the incapacitated pilot via the flight deck controls. Each recorded control input is compared to the corresponding expected control input (e.g., how the pilot should perform under these conditions) to identify deviant control input. If the recorded control input sufficiently deviates from expected performance, the system provides feedback to the pilot, co-pilot, or crew alerting to the deviant control input (e.g., which may be overridden or may require confirmation or resolution of the pilot's incapacitation state for execution).

In some embodiments, expected control inputs are tied to the current flight segment of the flight plan, e.g., takeoff, climb, cruise, descent, landing.

In some embodiments, expected control inputs are received from a ground control facility (e.g., via controller-pilot data link communications (CPDLC)).

In some embodiments, the flight deck controls provide feedback upon determination by the pilot monitors of a positive (e.g., non-adverse) change in the adverse incapacitation state of the pilot.

In some embodiments, the deviant control input is submitted through particular flight deck controls. The control input tracking system transfers control authority to automated systems (e.g., the aircraft autopilot), overriding the deviant control input until the incapacitated pilot provides confirmation of the deviant control input via alternative flight deck controls or methods.

In some embodiments, the flight deck controls provide feedback to another aircraft operator, e.g., a co-pilot, first officer, or other crewmember.

In some embodiments, the flight deck controls require conformation of the deviant control input from the other operator prior to execution of the control input.

In some embodiments, the control input tracking system assigns each recorded control input a priority level, comparing recorded control inputs to expected control inputs based on the assigned priority levels.

In some embodiments, recorded control inputs are prioritized based on one or more of: safety impact associated with deviance of the recorded control input from its corresponding expected input; whether the recorded control input is mission-critical; and/or the extent to which the recorded control input is reversible or recoverable.

In some embodiments, certain recorded control inputs are associated with a specific control location, e.g., the location of the corresponding flight deck controls within the cockpit or cabin. The pilot monitors (e.g., eye trackers) provide updates of the pilot's gaze direction, e.g., what the pilot is looking at at a given moment. Deviant control input may be identified if the pilot's gaze direction deviates from the control location of the recorded control input (e.g., the pilot is engaging a flight deck control while their visual attention is directed elsewhere).

In some embodiments, the threshold level for determining whether deviant recorded control input is sufficiently deviant to warrant feedback, override, and/or other response from the control input tracking system is based on the aircraft's current flight segment, the safety impact or mission criticality of the recorded control inputs, and/or the current incapacitation state of the pilot.

In some embodiments, the stored expected control inputs are associated with one or more automated checklists.

In a further aspect, a method for tracking control inputs from a potentially incapacitated aircraft pilot or operator is also disclosed. In embodiments, the method includes providing a control input tracking system with expected control inputs (e.g., expected control input procedure sets), wherein each expected control input corresponds to a flight deck control (e.g., via which the control input is normally submitted) and/or a particular segment of a flight plan. The method includes receiving from an aircraft-based pilot monitor an indication of an incapacitation state of a pilot or operator of the aircraft (e.g., incapacitated/not incapacitated (adverse/nominal); potentially or definitely incapacitated; fatigued, asleep, unresponsive, hypoxic, no longer incapacitated). The method includes, in response to the incapacitation state indicator, recording (via the control input tracking system) control inputs submitted by the incapacitated operator via the flight deck controls. The method includes identifying deviant control inputs submitted by the incapacitated pilot by comparing the recorded control inputs to their corresponding expected control inputs (e.g., how the pilot is expected to perform under the current conditions). The method includes, when the recorded control input sufficiently deviates from expected input, providing feedback to the pilot via the flight deck controls.

In some embodiments, the method includes providing feedback as to the deviant control input to another operator, e.g., a co-pilot, first officer, or crewmember of the aircraft.

In some embodiments, the method includes requiring confirmation of the deviant control input from the other operator before execution of the deviant control input.

In some embodiments, the method includes, when the deviant control input is submitted via a first flight deck control or set thereof, requiring confirmation of the deviant control input via an alternative flight deck control or set thereof before execution of the deviant control input.

In some embodiments, the method includes assigning, via the control input tracking system, a priority level to each recorded control input. Further, the method includes comparing the recorded control inputs to their corresponding expected control inputs in hierarchical order based on the assigned priority levels.

In some embodiments, the method includes assigning priority levels to recorded control inputs based on the safety-critical, mission-critical, or irreversible aspects of each control input. For example, more safety-critical or mission-critical and less reversible control inputs may be reviewed first.

In some embodiments, the method includes providing feedback to an incapacitated pilot only when the pilot monitor provides a subsequent indication of a positive change to an adverse incapacitation state, e.g., the pilot is no longer significantly incapacitated.

In some embodiments, each expected control input corresponds to a control location, e.g., a location of the flight deck controls via which the expected control input is submitted or what the pilot should ideally be looking at when submitting the expected control input. Further, the method includes providing, via the pilot monitor, gaze direction updates indicative of what the pilot is looking at at a given time. Further, the method includes identifying a deviant recorded control input if, at least in part, the pilot's gaze direction deviates from the control location of the expected control input (e.g., the pilot engages with a particular flight deck control while not looking at it).

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following:

A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination or sub-combination of two or more such features, along with any other features which may not necessarily be expressly described or inherently present in the instant disclosure.

Figure 1:
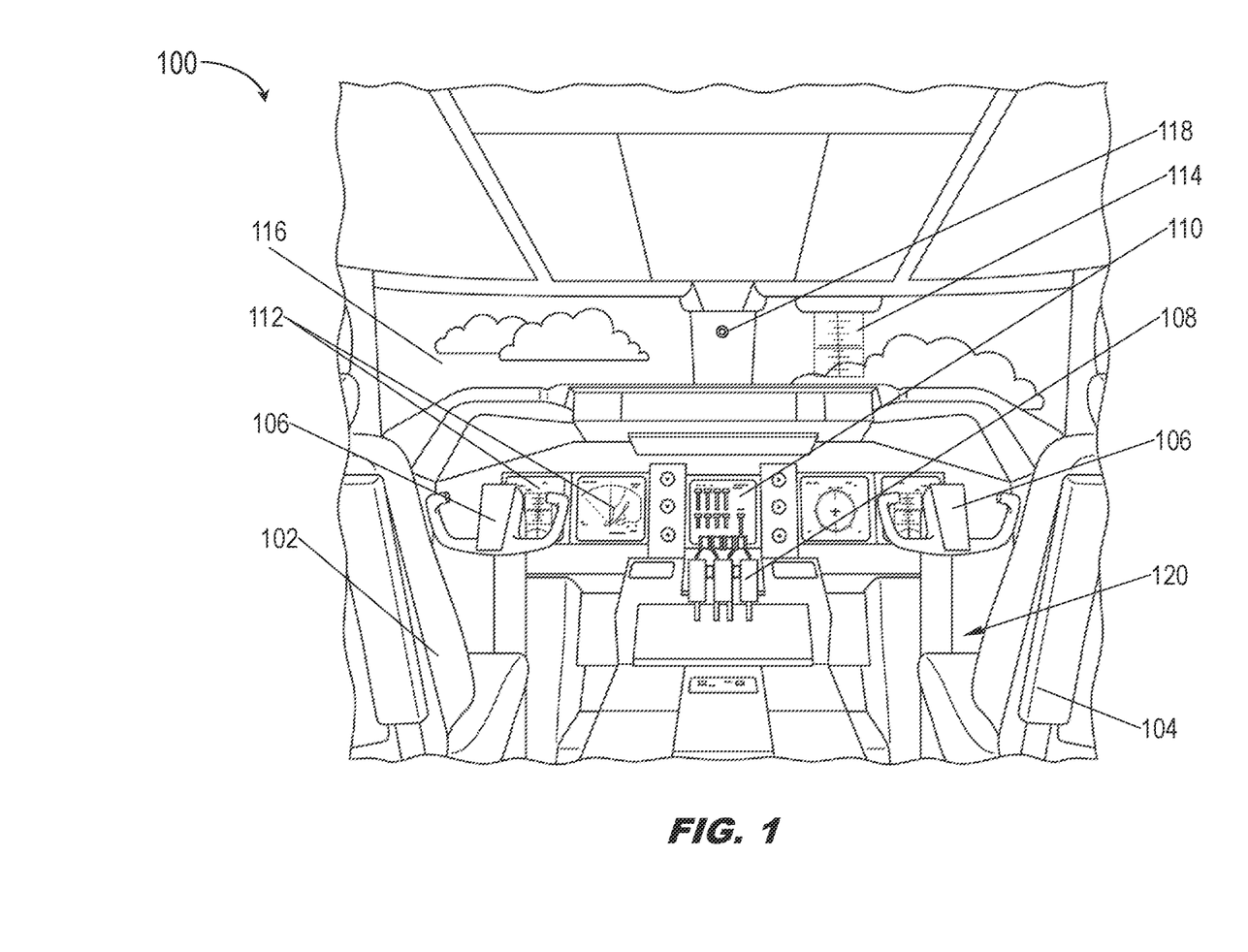
FIG. 1 is an illustration of a control space for an aircraft, the control space accommodating a pilot and co-pilot, flight deck controls, and a control input tracking system according to example embodiments of this disclosure.

Referring to FIG. 1, a control space 100 for an aircraft is disclosed. The control space 100 may include a pilot (e.g., seated in a left-side or pilot seat 102), co-pilot (e.g., seated in a right-side or co-pilot seat 104), control sticks 106, throttle controls 108, communications controls 110, flight displays 112, heads-up display 114 (HUD), windows 116, and gaze sensor 118.

In embodiments, the control space 100 of the aircraft may include an aircraft cockpit or any like space set aside for control of a vehicle or mobile platform by one or more operators (not shown; e.g., a pilot, co-pilot, and/or other crewmember) occupying a dedicated control position (e.g., the pilot seat 102 or co-pilot seat 104). For example, the operator may occupy either the pilot seat or co-pilot seat 104 and, throughout the totality of a flight sequence (e.g., through taxi, takeoff, climb, cruise, descent, landing, and taxi segments of a commercial aircraft) directly maneuver (or otherwise exercise primary control over) the aircraft, e.g., via the control stick 106, throttle controls 108, or other flight deck controls located in the control space 100 and configured for engagement by the operator.

Similarly, the operator may maintain situational awareness throughout the flight sequence based on visual intelligence. In embodiments, the operator may gain awareness as to the current status of the aircraft by viewing the flight displays 112 (e.g., primary flight displays (PFD), navigational displays, instrumentation displays) and/or the HUD 114. Some or all of the flight displays 112 or HUD 114 may be interactive touchscreens allowing the operator to engage with a touch-sensitive display surface and either adjust the information being displayed or exercise control over the aircraft (or one or more components or subsystems thereof).

In embodiments, the flight displays 112 may be implemented using any of a variety of display technologies, including CRT, LCD, organic LED, dot matrix display, and others. The flight displays 112 may be configured to display various types of flight-related and/or mission-related information. Further, in embodiments the operator may enhance situational awareness by looking through the windows 116 (e.g., forward windows, side windows). For example, the operator may use the windows 116 to enhance situational awareness by establishing positive visual identification of underlying terrain and natural or astronomical features (e.g., the position of the sun, moon, or stars), manmade landmarks (e.g., airport facilities, manmade obstacles), and/or proximate air traffic (e.g., manned aircraft reporting a position, unmanned aircraft not otherwise reporting a position).

In embodiments, throughout the flight sequence, from initial to final taxiing, the operator may engage with the control space 100 of the aircraft according to detectable routines or patterns. For example, the operator may be positioned in the pilot seat 102, physically engaging with the control stick 106 and throttle controls 108 via motion of the hand, arm, and/or torso. Similarly, the operator may, from their position in the pilot seat 102, visually engage with focus targets, e.g., physical controls, flight displays 112, HUD 114, and windows 116 by directing their gaze in the direction of each focus target in order to focus their vision and attention thereon.

In embodiments, the operator may additionally engage with electronic flight bags (EFB) or other like mobile devices not physically incorporated into the control space 100 of the aircraft but introduced therein by the operator and connected (e.g., via physical or wireless link) to the flight control system. For example, the operator occupying the pilot seat 102 may provide a tablet or like mobile communications device configured for displaying additional visual intelligence. In embodiments, the mobile device may occupy additional space (120) not already occupied by physical controls, windows 116, or display surfaces (112, 114). For example, the tablet may be attached to the operator's knee (e.g., via a kneeboard), carried in the operator's lap, mounted on a center console, or otherwise occupying a space 120 low in the operator's field of view (relative to the operator).

In embodiments, the flight displays 112 may further be configured to display operational context of various types and formats. For example, an airborne aircraft (e.g., a target) may be detected. The airborne aircraft (e.g., or indicator/s thereof) may be displayed on the flight displays 112. In response to the displayed operational context, the aircraft operator may gaze toward the flight displays 112 (e.g., toward specific portions thereof). A pattern of the gaze may provide a biomarker of the operator. In embodiments, the gaze sensor 118 may capture an image stream of the eye/s of the operator visually engaging with the flight displays 112 and/or other control interfaces throughout the control space 100. The gaze sensor 118 may include any suitable sensor, such as, but not limited to, a camera-based gaze sensor capturing a video stream of one or both eyes of the operator. In embodiments, the captured video stream may then be provided to an operator monitor for analysis as described below.

Broadly speaking, embodiments of the inventive concepts disclosed herein are directed to systems and methods for tracking control inputs from aircraft pilots, co-pilots or operators who may be physiologically or otherwise incapacitated, and determining whether these control inputs are unintentional inputs based on their deviation from expected control inputs under equivalent flight conditions. Control inputs from a potentially incapacitated pilot are recorded and compared with expected inputs; if the recorded control inputs sufficiently deviate from expected behavior alerts may be generated, e.g., for ground control or when the pilot has recovered. If the pilot is assisted by a co-pilot or other crewmembers, e.g., on commercial or passenger aircraft, other crewmembers may be alerted to the deviant control input in real time or near real time and may be required to confirm the input before executed by flight control systems.

Figure 2:
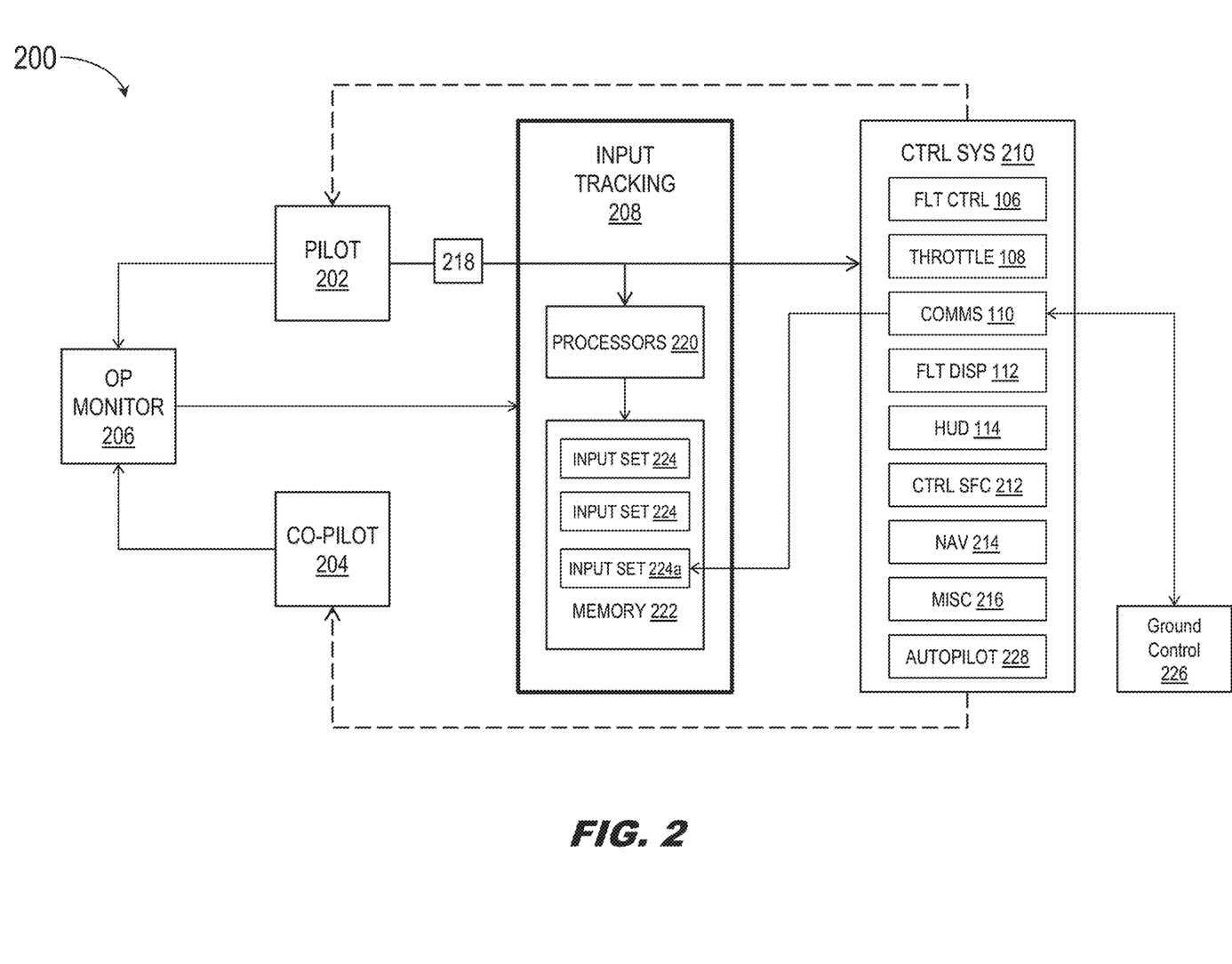
FIG. 2 is a block diagram illustrating the aircraft-based control input tracking system of FIG. 1.

Referring now to FIG. 2, the aircraft 200 is disclosed. The aircraft 200 may include a pilot 202 (e.g., captain), co-pilot 204 (e.g., first officer), operator monitors 206, and control input tracking system 208.

In embodiments, the pilot 202 (and/or co-pilot 204) may directly control operations of and aboard the aircraft 200 via direct control input provided to aircraft control systems 210. For example, by physically engaging with mechanical switches, buttons, dials (or with touch-sensitive display surfaces) or by providing verbal commands to voice-activated systems, the pilot 202 may operate and/or interact with control sticks 106; throttle controls 108; communications controls 110 (e.g., for intraship, air-to-air, air-to-ground, beacon, transponder, and other like communications systems); flight displays 112; HUD 114; control surfaces 212 (e.g., flaps, ailerons, rudders, landing gear); navigational systems 214; and/or other cockpit controls or miscellaneous systems 216 (e.g., fire extinguishers, circuit breakers). In some embodiments, the pilot 202 may be a pilot-in-command (PIC) or pilot flying (PF), and the co-pilot 204 may be a pilot monitoring (PM). In other embodiments, the pilot 202 may be the sole operator of the aircraft 200.

In embodiments, operator monitors 206 may monitor the pilot 202 and/or co-pilot 204 for signs of physiological incapacitation. For example, the operator monitors 206 may observe a variety of physiological parameters, e.g., gaze directions, eye movement, body temperature, cardiac activity, blood oxygen and pressure, to assess in real time or near real time the current capacity of the pilot 202 and co-pilot 204 (e.g., their overall health, well-being, and ability to perform their duties as PF/PM). Based on these parameters the operator monitors 206 may issue incapacitation state indicators indicative of a current incapacitation state of the pilot 202. For example, incapacitation state indicators may indicate that the pilot 202 is currently healthy and alert (e.g., a nominal incapacitation state), or indicate that the pilot may potentially be fatigued, hypoxic, or otherwise incapacitated (e.g., with respect situational awareness or reflexes) in a way that may impede the performance of their duties (e.g., an adverse incapacitation state).

In embodiments, the operator monitors 206 may alert the control input tracking system 208 to an adverse incapacitation state of the pilot 202. For example, incapacitation states determined by the operator monitors 206 may include broad determinations that the pilot may be potentially incapacitated, is incapacitated, or is not incapacitated; alternatively, incapacitation states may be more precise (e.g., depending on the precision of the operator monitors) determinations that a pilot is fatigued, unresponsive, asleep, hypoxic, or recovered from a prior incapacitation state. In some embodiments, the operator monitors 206 may determine (e.g., on a preliminary basis) that the pilot is potentially incapacitated (e.g., a change in incapacitation state) and subsequently confirm or verify the new adverse incapacitation state. Alternatively, the operator monitors may subsequently determine that, contrary to the preliminary determination, the pilot 202 is likely not incapacitated (or, e.g., has likely recovered from said incapacitation), and the adverse change in incapacitation state may be reversed.

In embodiments, when the operator monitors 206 indicates an adverse incapacitated state with respect to the pilot 202, the control input tracking system 208 may record and review any control input 218 provided to the control systems 210 by the pilot. For example, the control input tracking system 208 may be in communication with the control systems 210 and may log any control input associated with the adverse incapacitation state: any physical engagement of a button, dial, switch, or touch-sensitive display surface; any verbal or gesture-based control input (e.g., detectable and/or decodable via microphones or cameras within the control space 100).

In embodiments, the control input tracking system 208 may include processors 220 and memory 222. For example, the memory 222 may store sets of expected control inputs 224. Expected control inputs may include sets of sequences of control inputs expected from the pilot 202 and/or co-pilot 204 based on specific flight segments and/or portions thereof. For example, sets of expected control inputs 224 may include automated procedure checklists to be followed, e.g., during taxi, takeoff, climb, cruise, descent, and/or landing segments. In some embodiments, expected control inputs 224 may account for an adverse incapacitation state with respect to the pilot 202, e.g., procedure sets or checklists to be followed by the co-pilot 204 in the event of a particular incapacitation state on the part of the pilot. In some embodiments, some sets of expected control inputs 224a may be received from ground control 226 via communications systems, e.g., via Controller-Pilot Data Link Communications (CPDLC).

In embodiments, the control input tracking system 208 may identify deviant control input submitted by a potentially incapacitated pilot 202, e.g., unintentional control input that may present a hazard to the aircraft 200 or control input otherwise associated with an adverse incapacitation state. For example, when the operator monitors 206 indicate potential incapacitation of the pilot 202, the control input tracking system 208 may record any control inputs 218 submitted by the pilot. Recorded control inputs may be stored to memory 222 and compared to equivalent sets of expected control inputs 224, 224a. In embodiments, evaluation of recorded control inputs 218 may occur in real time or near real time. For example, recorded control inputs 218 may be compared to expected control inputs 224, 224a to determine the extent to which a given recorded control input aligns with, or deviates from, the corresponding expected control input. Further, any deviations of recorded control inputs 218 from their corresponding expected control inputs 224, 224a may be prioritized for assessment (e.g., either by the control input tracking system 208 or predetermined prior to commencement of the flight plan) in light of, e.g., a safety impact of deviations from the expected control input; the mission criticality of an abnormal control input; the current flight segment; and/or the reversibility of the abnormal control input. For example, any deviation from expected behavior generally by the pilot 202 may be viewed as potentially far more hazardous during takeoff or landing phases, when the pilot, co-pilot 204, and/or other crewmembers must be particularly focused on multiple safety-critical tasks or duties (e.g., the aforementioned Air India Express flight, wherein abnormal control input by a momentarily incapacitated captain during the crucial takeoff phase, and failure to detect or respond to said input by the first officer, both jeopardized a safe takeoff and significantly damaged the aircraft to require its later diversion). Similarly, some recorded control inputs 218 may be more reversible and less consequential, either immediately or in the short term, than others and may therefore be assessed as less critical and/or less subject to prompt alert and/or resolution of the abnormal input. If, for example, the pilot 202 were to inadvertently disengage synthetic vision system (SVS) services to the primary flight display at cruising altitude, the overall flight plan and safety of the aircraft 200 would likely be unaffected and the anomalous input would be easily resolved by re-engaging SVS. By contrast, as the Air India Express incident demonstrated, a sudden reduction in thrust caused by the captain's abnormal control input would be reversible (and indeed should have been reversed), but as the aircraft proceeds down the runway the capability of reversal (e.g., restoration of thrust) to ensure a safe takeoff diminishes with each passing second as the aircraft runs out of available runway while attempting, and failing, to reach takeoff speed. In some embodiments, threshold levels for deviant recorded control input 218 may further account for the level or type of incapacity of the pilot 202, if this information is available from the operator monitors 206.

In embodiments, when a deviant recorded control input 218 meets or exceeds threshold levels (e.g., with respect to criticality and/or flight segment as discussed above), the control input tracking system 208 may alert the pilot 202, co-pilot 204, and/or ground control 226 that an abnormal control input was entered. For example, if the pilot 202 is a solo operator, the anomalous control input may be logged by ground control 226 for later review. In some embodiments, the control input tracking system 208 may direct control systems 210 and/or flight deck controls to alert the pilot 202 with sufficient intensity and/or force to account for the determined incapacitation state, e.g., visual alerts, aural alerts, tactile alerts (e.g., stick shakers, speedbumps). In some embodiments, e.g., if the deviant control inputs are non-critical and the pilot 202 is a solo operator, the control input tracking system 208 may alert the pilot to deviant control inputs once the operator monitors 206 determine a positive change in incapacitation state, e.g., that a previously determined adverse incapacitation state no longer applies.

In some embodiments, the pilot 202 (or a co-pilot 204 not associated with a current adverse incapacitation state) may be required to confirm an abnormal control input entered to the control systems 210 before the control input is executed (e.g., if the control input is sufficiently deviant, critical, and/or irreversible). For example, the pilot 202 may be alerted to the abnormal control input and required to reassert (e.g., "are you sure?"), or the co-pilot 204 may be required to assent to the abnormal control input prior to execution. In some embodiments, e.g., if the pilot 202 is a solo operator, the alert may be forwarded to ground control 226, who may elect to overrule the deviant control input.

In some embodiments, the control input tracking system 208 may prioritize the review of recorded control inputs 218, e.g., if the control input tracking system is assessing recorded control inputs in real time or near real time or the pool of recorded control inputs is large or complex. For example, the control input tracking system 208 may prioritize the review of recorded control inputs 218 to safety-critical or aviation-critical systems (e.g., control sticks 106, throttle controls 108, control surfaces 212) over the review of control inputs to mission-critical systems or those control systems 210 not directly affecting the immediate safety of the aircraft 200 (e.g., navigational systems 214, communications controls 110, flight displays 112, HUD 114), e.g., "aviate, navigate, communicate".

In some embodiments, the control systems 210 may assume full or partial control authority from the pilot 202 if a sufficiently adverse incapacitation state is determined and associated control inputs are sufficiently deviant. For example, if the operator monitors 206 determine an adverse incapacitation state of the pilot 202 (e.g., experiencing probable or definite hypoxia, fatigue, or a similar physiological episode), and one or more recorded control inputs 218 submitted by the pilot 202 are determined to deviate at or above threshold levels, e.g., in terms of their safety impact, criticality and/or irreversibility, the control input tracking system 208 may shift control authority to system automation, e.g., an autopilot system 228, until the operator monitors 206 determine that the current incapacitation state of the pilot 202 has sufficiently resolved. If, for example, the autopilot 228 is directing an initial climb to a previously input target cruising altitude and a hypoxic pilot 202 pushes the control sticks 106 downward (e.g., to descend), the control input tracking system 208 may direct the autopilot 228 to override the deviant control input from the pilot and continue the prescribed climb. Further, the control input tracking system 208 would provide the pilot with a warning as to the reason for the override, and allow for the pilot to take back control authority from the control input tracking system via a dissimilar flight deck control or method (e.g., a touchscreen display input, another physical input button on the flight deck, or some other form of providing a particular form of control input other than the flight deck control via which the originally deviant control input was received). In embodiments, if the pilot remains unresponsive to an override and/or the adverse incapacitation state persists, the control input tracking system 208 may initiate additional emergency procedure steps, e.g., automatic path planning, reporting the incapacity/emergency state to air traffic control, emergency descent to safe altitude, or emergency landing.

Figure 3:
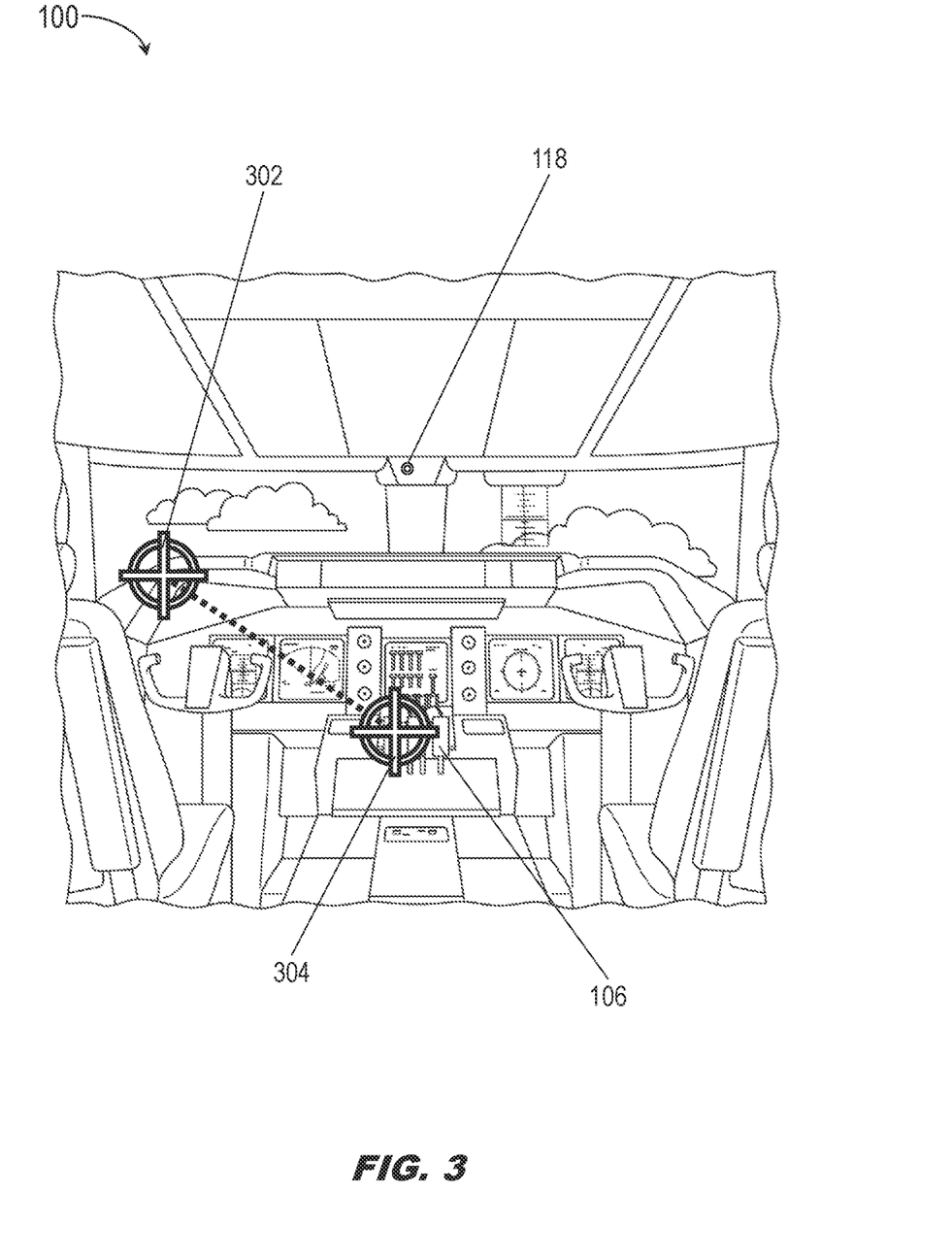
FIG. 3 is an illustration of the control space of FIG. 1 showing gaze tracking operations of the control input tracking system of FIG. 1 according to example embodiments of this disclosure.

Referring also to FIG. 3, the control space 100 of the aircraft 200 (see FIG. 2) is shown.

In some embodiments, the control input tracking system 208 may receive gaze tracking information from the operator monitors 206. For example, the control input tracking system 208 may correlate gaze tracking information with respect to recorded control inputs 218 submitted by the pilot and evaluate particular control inputs as deviant if the gaze tracking information does not correspond to the control input. In embodiments, referring also to FIG. 1, each of the control systems 210 may each correspond to a particular control location, e.g., a location of a corresponding flight deck control within the control space 100 of the aircraft 200 (e.g., control sticks 106, throttle controls 108, communications controls 110, flight displays 112, HUD 114, navigational systems 214). Accordingly, the operator monitors 206 (e.g., via gaze sensor 118) may further track the gaze direction of the pilot 202, or what the pilot is looking at from moment to moment.

In embodiments, some or all recorded control inputs 218 submitted by the pilot 202 may be associated with gaze information 302 from the operator monitors 206 (e.g., where the pilot's gaze is directed at a given time). For example, if the pilot 202 engages with the throttle controls 108, the operator monitors 206 may verify that the pilot 202 was looking at the throttle controls 108 (e.g., control location 304) at the time of engagement, e.g., at the time the recorded control input was submitted. If, however, a recorded control input 218 is of sufficient safety impact, mission criticality, or irreversibility, the control input tracking system 208 may assess the recorded control input as deviant if the corresponding gaze information 302 does not match, or sufficiently deviates from, the control location 304 corresponding to the control input (e.g., if the pilot is not looking anywhere near the particular flight deck controls with which they are engaging). For example, if the control input tracking system 208 records the pilot 202 as engaging with a fire extinguisher system (irreversible once activated) but the operator monitor 206 provides gaze information 302 indicating the pilot was not looking at the fire extinguisher system at the time (e.g., a different control location 304), the control input tracking system 208 may treat the control input 218 as unintentional (e.g., indicative of potential incapacitation, even if the current incapacitation state of the pilot 202 is nominal) and require confirmation of the control input by the pilot or co-pilot 204 prior to execution.

Figure 4:
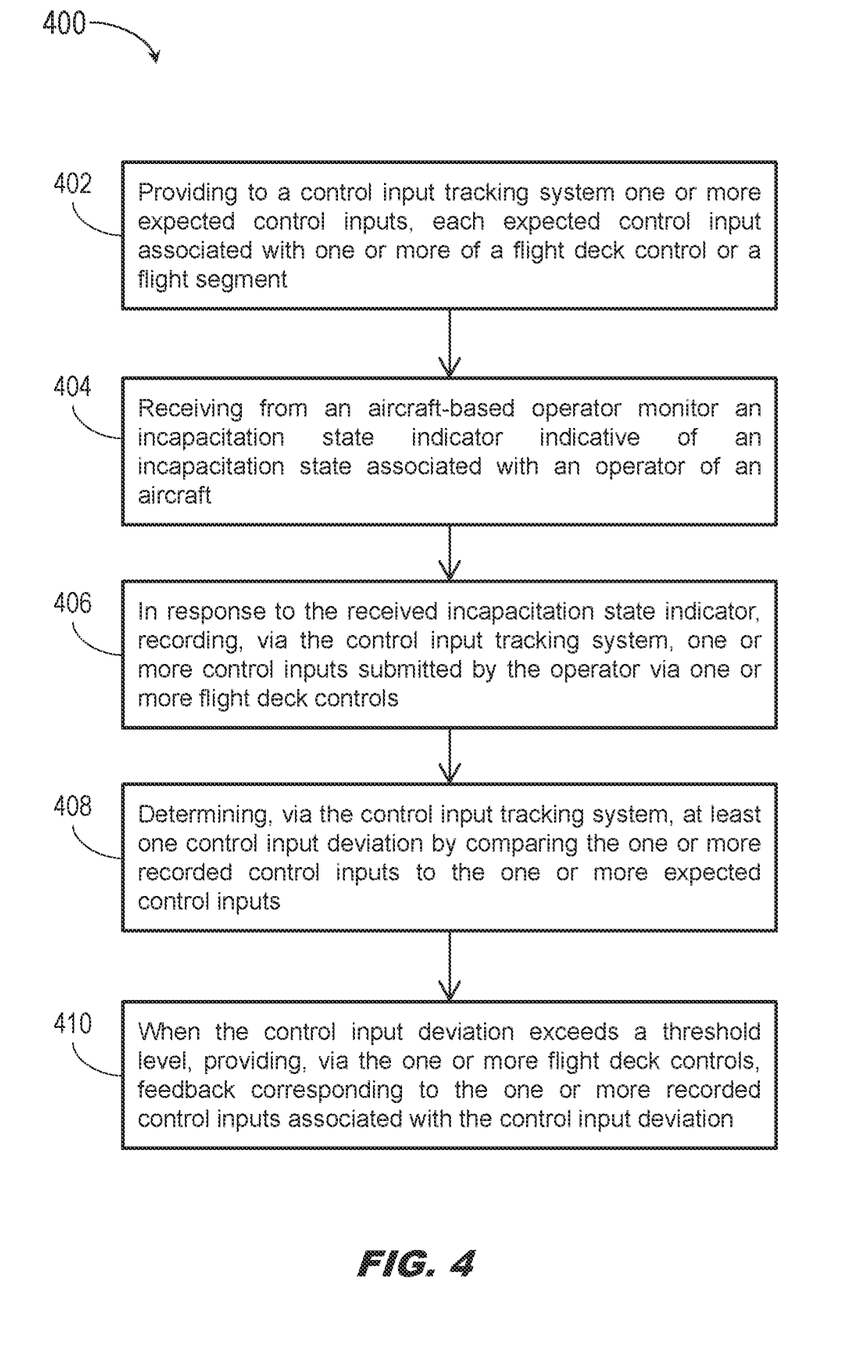
FIG. 4 is a flow diagram illustrating a method for tracking and verifying questionable control inputs from potentially incapacitated aircraft operators, according to example embodiments of this disclosure.

Referring now to FIG. 4, the method 400 may be implemented by the control input tracking system 208 and may incorporate the following steps.

At a step 402, the control input tracking system is provided with sets of expected control inputs, e.g., for storage to memory. For example, expected control inputs may include automated checklists to be followed by a pilot or co-pilot, e.g., expected or required engagements with flight deck controls and/or other aircraft system/subsystem controls for a particular flight segment or scenario (e.g., in the event of a pilot incapacitation). In some embodiments, expected control inputs may be received from a ground control station, e.g., via CPDLC.

At a step 404, aircraft operator monitors provide the control input tracking system with incapacitation state indicators indicative of an incapacitation state (e.g., or change in incapacitation state) of the pilot. For example, the incapacitation state may be nominal (no incapacitation) or adverse, indicating that the pilot may be potentially or definitely physiologically incapacitated (e.g., that the pilot is asleep, fatigued, hypoxic, unresponsive). For example, the operator monitors may indicate potential incapacitation, e.g., on a preliminary basis; alternatively, the operator monitors may confirm a preliminary finding by determining incapacitation with greater certainty. In some embodiments, the operator monitors may reverse a preliminary adverse incapacitation state by determining that the pilot is not incapacitated.

At a step 406, in response to the incapacitation state indicator (e.g., indicative of an adverse incapacitation state), the control input tracking system records control inputs submitted by the potentially incapacitated pilot, e.g., via cockpit flight deck controls, touch-sensitive displays, and/or other system and subsystem controls.

At a step 408, the control input tracking system identifies deviant or potentially inadvertent control input submitted by the incapacitated pilot by comparing recorded control inputs to corresponding expected control inputs. For example, the control input tracking system may prioritize the review of some recorded control inputs over others based on, e.g., a safety impact of the deviation of the recorded control input from the corresponding expected control input, the mission criticality of the recorded control input, the reversibility of the recorded control input, the current flight segment, or other criteria. Similarly, threshold levels for a deviant control input may depend on the incapacitation state of the pilot, the current flight segment, the safety impact of the deviation, and/or the criticality or reversibility of a particular control input or set thereof.

At a step 410, when a recorded control input deviates from the expected control input at or above a threshold level, the control input tracking system may direct the flight deck controls to provide feedback to the pilot or to another crewmember. For example, the flight deck controls may provide feedback to the pilot (accounting for potential incapacitation) to inform the pilot of the deviant control input, or require confirmation before the control input is executed. In some embodiments, feedback will be provided to, or confirmation of a deviant control input required from, a co-pilot or other crewmember. In other embodiments, deviant control input submitted via a particular flight deck control may require confirmation via a different flight deck control. Feedback may be visual, aural, or tactile. In some embodiments, the flight deck controls may provide feedback only after an adverse incapacitation state (e.g., fatigue, hypoxia, unresponsiveness) is determined to have been resolved (e.g., nominal incapacitation state).

CONCLUSION

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

We claim:

1. An aircraft-based system for tracking control inputs, comprising:

at least one processor operatively coupled to one or more flight deck controls of an aircraft and to an operator monitor of the aircraft;
and
a memory in data communication with the at least one processor and configured for storage of a plurality of expected control inputs;
wherein the at least one processor is configured to:
receive at least one indication of an incapacitation state from the operator monitor, the incapacitation state associated with an operator of the aircraft;
in response to the indication, record one or more control inputs submitted by the operator via the one or more flight deck controls;
determine at least one control input deviation by comparing the one or more recorded control inputs to one or more expected control inputs of the plurality of expected control inputs;
and
when the at least one control input deviation exceeds a threshold level, direct the one or more flight deck controls to provide feedback corresponding to the associated recorded control input.

2. The aircraft-based system of claim 1, wherein the one or more expected control inputs are associated with a current flight segment of the aircraft.

3. The aircraft-based system of claim 1, wherein the one or more expected control inputs are received from a ground control station.

4. The aircraft-based system of claim 1, wherein the at least one incapacitation state indicator is a first incapacitation state indicator, and:
the at least one processor is configured to direct the one or more flight deck controls to provide feedback upon receiving at least one second incapacitation state indicator from the operator monitor, the at least one second incapacitation state indicator indicative of a change to the incapacitation state associated with the operator.

5. The aircraft-based system of claim 1, wherein:
the at least one control input deviation is associated with at least one recorded control input submitted via a first flight deck control of the one or more flight deck controls;
and
wherein the at least one processor is configured to, when the control input deviation exceeds the threshold level:
transfer control authority over the one or more flight deck controls to at least one automated system of the aircraft;
and
return the control authority to the operator in response to a confirmation of the at least one recorded control input submitted by the operator via at least one second flight deck control of the one or more flight deck controls.

6. The aircraft-based system of claim 1, wherein the operator is a first operator, and the at least one processor is configured to direct the one or more flight deck controls to provide the feedback to at least one second operator of the aircraft.

7. The aircraft-based system of claim 6, wherein the feedback requires confirmation from the at least one second operator for execution of the recorded control input.

8. The aircraft-based system of claim 1, wherein:
each recorded control input is associated with a priority level;
and
the at least one processor is configured to compare the one or more recorded control inputs to the one or more expected control inputs in hierarchical order based on the associated priority level of each recorded control input.

9. The aircraft-based system of claim 8, wherein each recorded control input is associated with the priority level based on one of more of:
a safety impact associated with a deviation of the recorded control input from the corresponding expected control input;
a mission criticality associated with the recorded control input;
or
a reversibility of the recorded control input.

10. The aircraft-based system of claim 1, wherein:
the one or more recorded control inputs include at least one first control input associated with a control location within the aircraft;
and
wherein the at least one processor is configured to:
receive from the operator monitor a gaze direction of the operator, the gaze direction corresponding to the at least one first control input;
and
determine the at least one deviation by comparing the gaze direction and the associated control location.

11. The aircraft-based system of claim 1, wherein the threshold level is based on at least one of:
a current flight segment of the aircraft;
a criticality level of the one or more recorded control inputs:
or
the incapacitation state associated with the indication received from the operator monitor.

12. The aircraft-based system of claim 1, wherein the one or more expected control inputs are associated with at least one automated checklist.

13. A method for tracking aircraft control inputs, comprising:
providing to a control input tracking system one or more expected control inputs, each expected control input associated with one or more of a flight deck control or a flight segment;
receiving from an aircraft-based operator monitor an incapacitation state indicator indicative of an incapacitation state associated with an operator of an aircraft;
in response to the received incapacitation state indicator, recording, via the control input tracking system, one or more control inputs submitted by the operator via one or more flight deck controls;
determining, via the control input tracking system, at least one control input deviation by comparing the one or more recorded control inputs to the one or more expected control inputs;
and
when the control input deviation exceeds a threshold level, providing, via the one or more flight deck controls, feedback corresponding to the one or more recorded control inputs associated with the control input deviation.

14. The method of claim 13, wherein the operator is a first operator of the aircraft and:
when the control input deviation exceeds a threshold level, providing, via the one or more flight deck controls, feedback corresponding to the one or more recorded control inputs associated with the control input deviation includes:
providing, via the one or more flight deck controls, feedback to a second operator of the aircraft.

15. The method of claim 14, wherein providing, via the one or more flight deck controls, feedback to a second operator of the aircraft includes:
requiring a confirmation by the second operator prior to execution of the one or more recorded control inputs associated with the control input deviation.

16. The method of claim 14, wherein:
recording, via the input tracking system, one or more control inputs submitted by the operator via one or more flight deck controls includes recording one or more first control inputs submitted via one or more first flight deck controls, the one or more first control inputs associated with the control input deviation;
and
wherein, when the control input deviation exceeds a threshold level, providing, via the one or more flight deck controls, feedback corresponding to the one or more recorded control inputs associated with the control input deviation includes:
requiring a confirmation of the one or more first control inputs via one or more second flight deck controls prior to execution of the one or more recorded control inputs associated with the control input deviation.

17. The method of claim 13, wherein:
recording to an input tracking system one or more control inputs submitted by the operator via one or more flight deck controls includes associating a priority level with each recorded control input;
and
determining, via the input tracking system, at least one control input deviation by comparing the one or more recorded control inputs to the one or more expected control inputs includes comparing the one or more recorded control inputs in hierarchical order based on the associated priority level of each recorded control input.

18. The method of claim 17, wherein assigning a priority level to each recorded control input includes assigning a priority level to each recorded control input based on at least one of:
- a safety impact associated with a deviation of the recorded control input from the corresponding expected control input;
- a mission criticality associated with the recorded control input;
- or
- a reversibility of the recorded control input.

19. The method of claim 13, wherein the incapacitation state indicator is a first incapacitation state indicator indicative of an adverse incapacitation state and wherein providing, via the one or more flight deck controls, feedback corresponding to the one or more recorded control inputs associated with the control input deviation includes:
- receiving, via the operator monitor, at least one second incapacitation state indicator indicative of a non-adverse incapacitation state associated with the operator; and
- providing to the operator, via the one or more flight deck controls, feedback corresponding to the one or more recorded control inputs associated with the control input deviation.

20. The method of claim 13, wherein:
providing to an input tracking system one or more expected control inputs includes:
- providing at least one first expected control input associated with a control location;

wherein recording via the input tracking system one or more control inputs submitted by the operator via one or more flight deck controls includes:
- receiving from the operator monitor at least one gaze direction of the operator associated with the one or more recorded control inputs;

and
wherein determining, via the input tracking system, at least one control input deviation includes:
- comparing the gaze direction associated with the one or more recorded control inputs and the control location associated with the at least one first expected control input.

* * * * *